(12) United States Patent
Choi et al.

(10) Patent No.: US 8,285,353 B2
(45) Date of Patent: *Oct. 9, 2012

(54) SYSTEM FOR ANALYZING TISSUE PERFUSION USING CONCENTRATION OF INDOCYANINE GREEN IN BLOOD

(75) Inventors: Chulhee Choi, Daejeon (KR); Yujung Kang, Daejeon (KR); Myunghwan Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 557 days.

This patent is subject to a terminal disclaimer.

(21) Appl. No.: 12/445,212

(22) PCT Filed: Jul. 11, 2007

(86) PCT No.: PCT/KR2007/003355
§ 371 (c)(1),
(2), (4) Date: Apr. 10, 2009

(87) PCT Pub. No.: WO2008/044822
PCT Pub. Date: Apr. 17, 2008

(65) Prior Publication Data
US 2010/0036217 A1 Feb. 11, 2010

(30) Foreign Application Priority Data
Oct. 11, 2006 (KR) .................. 10-2006-0099033

(51) Int. Cl.
*A61B 5/00* (2006.01)
(52) U.S. Cl. ........ 600/329; 600/310; 600/312; 600/476; 600/479
(58) Field of Classification Search .................. 600/310, 600/312, 329, 476, 479
See application file for complete search history.

(56) References Cited

U.S. PATENT DOCUMENTS 4,269,636 A    5/1981   Rivoli et al. .................. 438/359
(Continued)

FOREIGN PATENT DOCUMENTS

EP           0 589 675 A2     3/1994
(Continued)

OTHER PUBLICATIONS

Costa, Rogerio A. et al., "Selective Occlusion of Subfoveal Choroidal Neovascularization in Pathologic Myopia Using a New Technique of Ingrowth Site Treatment," *Am. J. Ophthalmol.*, vol. 135:857-866 (2003).

(Continued)

*Primary Examiner* — Long V. Le
*Assistant Examiner* — Ellsworth Weatherby
(74) *Attorney, Agent, or Firm* — Nelson Mullins Riley & Scarborough LLP; EuiHoon Lee, Esq.

(57) ABSTRACT

The present invention relates, in general, to a system for analyzing tissue perfusion using the concentration of indocyanine green and a method of measuring the perfusion rate using the system and, more particularly, to a system for measuring tissue perfusion by injecting indocyanine green into a living body, detecting variation in the concentration of indocyanine green with the passage of time, and analyzing the detected variation, and a method of measuring the perfusion rate using the system. The present invention provides a method of measuring perfusion in a living body, which enables accurate measurement for respective regions in a wide range from a perfusion rate decreased to less than 10% of normal perfusion to a perfusion rate increased to greater than normal perfusion using the above-described mechanism of ICG in a living body, which cannot be conducted using the conventional technology.

12 Claims, 5 Drawing Sheets

U.S. PATENT DOCUMENTS

| | | | |
|---|---|---|---|
| 4,454,647 A | 6/1984 | Joy et al. | 29/576 |
| 4,478,655 A | 10/1984 | Nagakubo et al. | 148/175 |
| 4,642,883 A | 2/1987 | Sakurai et al. | 438/362 |
| 4,655,875 A | 4/1987 | Wada et al. | 438/514 |
| 4,819,052 A | 4/1989 | Hutter | 257/378 |
| 4,980,747 A | 12/1990 | Hutter et al. | 357/50 |
| 5,374,569 A | 12/1994 | Yilmaz et al. | 437/34 |
| 5,410,175 A | 4/1995 | Kyomasu et al. | 257/458 |
| 5,420,061 A | 5/1995 | Manning | 438/218 |
| 5,506,431 A | 4/1996 | Thomas | 365/185.15 |
| 5,525,824 A | 6/1996 | Himi et al. | 257/370 |
| 5,557,135 A | 9/1996 | Hashimoto | 257/308 |
| 5,668,397 A | 9/1997 | Davis et al. | 257/520 |
| 5,684,305 A | 11/1997 | Pearce | 257/48 |
| 5,807,783 A | 9/1998 | Gaul et al. | 438/406 |
| 5,883,413 A | 3/1999 | Ludikhuize | 257/343 |
| 5,892,264 A | 4/1999 | Davis et al. | 257/511 |
| 5,986,863 A | 11/1999 | Oh | 361/56 |
| 6,013,936 A | 1/2000 | Colt | 257/506 |
| 6,130,458 A | 10/2000 | Takagi et al. | 257/351 |
| 6,144,086 A | 11/2000 | Brown et al. | 257/510 |
| 6,163,052 A | 12/2000 | Liu et al. | 257/334 |
| 6,331,456 B1 | 12/2001 | Wu | 8/154 |
| 6,383,892 B1 | 5/2002 | Colt | 438/457 |
| 6,542,769 B2 | 4/2003 | Schwamm et al. | |
| 6,559,505 B1 | 5/2003 | Fallica | 257/350 |
| 6,631,286 B2 * | 10/2003 | Pfeiffer et al. | 600/473 |
| 6,657,262 B2 | 12/2003 | Patti | 257/370 |
| 6,740,958 B2 | 5/2004 | Nakazato et al. | 257/550 |
| 6,855,985 B2 | 2/2005 | Williams et al. | 257/338 |
| 6,900,091 B2 | 5/2005 | Williams et al. | 438/228 |
| 6,943,426 B2 | 9/2005 | Williams et al. | 257/500 |
| 7,009,271 B1 | 3/2006 | Thurgate et al. | 257/510 |
| 7,049,663 B2 | 5/2006 | Wang | 257/355 |
| 7,176,548 B2 | 2/2007 | Williams et al. | 257/500 |
| 7,183,610 B2 | 2/2007 | Pattanayak et al. | 257/333 |
| 7,268,045 B2 | 9/2007 | Hower et al. | 438/282 |
| 2001/0013636 A1 | 8/2001 | Dunn et al. | 257/565 |
| 2002/0008299 A1 | 1/2002 | Leonardi | 257/520 |
| 2002/0084506 A1 | 7/2002 | Voldman et al. | 257/511 |
| 2003/0107103 A1 | 6/2003 | Iwata et al. | 257/506 |
| 2003/0168712 A1 | 9/2003 | Shin et al. | 257/510 |
| 2003/0211036 A1 * | 11/2003 | Degani et al. | 424/1.11 |
| 2004/0026746 A1 | 2/2004 | Nakazawa et al. | 257/374 |
| 2004/0032005 A1 | 2/2004 | Williams et al. | 257/510 |
| 2004/0033666 A1 | 2/2004 | Williams et al. | 438/297 |
| 2005/0014324 A1 | 1/2005 | Williams et al. | 438/200 |
| 2005/0014329 A1 | 1/2005 | Williams et al. | 438/318 |
| 2005/0142724 A1 | 6/2005 | Williams et al. | 438/199 |
| 2005/0142791 A1 | 6/2005 | Williams et al. | 438/369 |
| 2005/0142792 A1 | 6/2005 | Williams et al. | 438/369 |
| 2005/0158939 A1 | 7/2005 | Williams et al. | 438/199 |
| 2005/0179111 A1 | 8/2005 | Chao | 257/510 |
| 2005/0189606 A1 | 9/2005 | Nakagawa | 257/500 |
| 2005/0272207 A1 | 12/2005 | Williams et al. | 438/261 |
| 2005/0272230 A1 | 12/2005 | Williams et al. | 438/510 |
| 2005/0287765 A1 | 12/2005 | Onai et al. | 438/438 |
| 2006/0076629 A1 | 4/2006 | Yilmaz | 257/378 |
| 2006/0134001 A1 * | 6/2006 | Frangioni | 424/9.6 |
| 2006/0175635 A1 | 8/2006 | Arai et al. | 257/197 |
| 2006/0223257 A1 | 10/2006 | Williams et al. | 438/202 |
| 2007/0013021 A1 | 1/2007 | Zhang | 257/500 |
| 2007/0132056 A1 | 6/2007 | Williams et al. | 257/510 |
| 2007/0158779 A1 | 7/2007 | Cannon et al. | 257/500 |
| 2007/0241421 A1 | 10/2007 | Liu et al. | 257/510 |
| 2007/0278568 A1 | 12/2007 | Williams et al. | 257/335 |
| 2007/0278612 A1 | 12/2007 | Williams et al. | 257/338 |
| 2008/0042232 A1 | 2/2008 | Williams et al. | 257/338 |
| 2008/0044978 A1 | 2/2008 | Williams et al. | 257/338 |
| 2008/0048287 A1 | 2/2008 | Williams et al. | 257/338 |
| 2008/0191277 A1 | 8/2008 | Disney et al. | 257/327 |
| 2008/0197408 A1 | 8/2008 | Disney et al. | 257/335 |
| 2008/0197445 A1 | 8/2008 | Disney et al. | 257/272 |
| 2008/0197446 A1 | 8/2008 | Disney et al. | 257/499 |
| 2008/0210980 A1 | 9/2008 | Disney et al. | 257/204 |
| 2008/0213972 A1 | 9/2008 | Disney et al. | 438/430 |
| 2008/0217699 A1 | 9/2008 | Disney et al. | 257/378 |
| 2008/0230812 A1 | 9/2008 | Disney et al. | 257/272 |
| 2008/0237656 A1 | 10/2008 | Williams et al. | 257/262 |
| 2008/0237704 A1 | 10/2008 | Williams et al. | 257/338 |
| 2008/0237706 A1 | 10/2008 | Williams et al. | 257/343 |
| 2008/0237782 A1 | 10/2008 | Williams et al. | 257/499 |
| 2008/0237783 A1 | 10/2008 | Williams et al. | 257/513 |
| 2008/0290449 A1 | 11/2008 | Williams et al. | 257/513 |
| 2008/0290450 A1 | 11/2008 | Williams et al. | 257/513 |
| 2008/0290451 A1 | 11/2008 | Williams et al. | 257/513 |
| 2009/0203993 A1 * | 8/2009 | Mangat et al. | 600/431 |

FOREIGN PATENT DOCUMENTS

| | | |
|---|---|---|
| EP | 1357598 A1 | 10/2003 |
| GB | 2 362 508 | 11/2001 |
| KR | 10-0456691 | 11/2008 |
| WO | WO-00/00080 A1 | 1/2000 |
| WO | WO-01/22870 A1 | 4/2001 |

OTHER PUBLICATIONS

Helisch, Armin et al., "Impact of Mouse Strain Differences in Innate Hindlimb Collateral Vasculature," *Arterioscler. Thromb. Vasc. Biol.*, vol. 26:520-526 (2006).

Holm, C. et al., "Intraoperative evaluation of skin-flap viability using laser-induced fluorescence of indocyanine green," *British Journal of Plastic Surgery*, vol. 55:635-644 (2002).

Morgan, Nicole Y. et al., "Real Time in Vivo Non-invasive optical Imaging Using Near-infrared Fluorescent Quantum Dots," *Acad. Radiol.*, vol. 12:313-323 (2005).

Sekimoto, M. et al., "Plasma volume estimation using indocyanine green with biexponential regression analysis of the decay curves," *Anaesthesia*, vol. 52:1166-1172 (1997).

* cited by examiner

Perfusion Rate (%/min)

SYSTEM FOR ANALYZING TISSUE PERFUSION USING CONCENTRATION OF INDOCYANINE GREEN IN BLOOD

RELATED APPLICATIONS

This application is a 35 U.S.C. §371 national stage filing of International Application No. PCT/KR2007/003355 filed on Jul. 11, 2007, which claims priority to, and the benefit of, Korean Patent Application No. 10-2006-0099033 filed on Oct. 11, 2006. The contents of the aforementioned applications are hereby incorporated by reference.

TECHNICAL FIELD

The present invention relates to a system for analyzing tissue perfusion and a method of measuring the perfusion rate using the system. More particularly, the present invention relates to a system for measuring tissue perfusion by injecting indocyanine green into a living body, detecting variation in the concentration of indocyanine green with the passage of time, and analyzing the detected variation, and a method of measuring the perfusion rate using the system.

BACKGROUND

The conventional tissue perfusion measuring method 'laser Doppler imaging' is a method of measuring the degree of scattering of laser light depending on the speed of blood flow in a skin surface, but has a shortcoming in that it is unsuitable for a method of measuring variation in the state in which blood flow is low because sensitivity is low when blood flow rate decreases to less than 20% of the normal of the blood flow rate.

Another conventional blood vessel imaging method 'X-ray blood vessel imaging (X-ray angiography)' shows X-ray images using a blood vessel contrast agent. However, it is a structural imaging technique that shows the configuration of the internal diameters of blood vessels, rather than the actual flow of blood (Helisch, A., Wagner, S., Khan, N., Drinane, M., Wolfram, S., Heil, M., Ziegelhoeffer, T., Brandt, U., Pearlman, J. D., Swartz, H. M. & Schaper, W. (2006) *Arterioscler. Thromb. Vasc. Biol.,* 26: 520-526). Accordingly, it is currently impossible to clinically measure the precise rate of tissue perfusion using this method.

The safety of a conventional blood vessel imaging method using indocyanine green (ICG angiography) has already been verified (Sekimoto, M., Fukui, M. & Fujita, K. (1997) Anaesthesia 52: 1166-1172), and the method has been clinically used for the detection of the formation of blood vessels in grafted skin (Holm, C., Mayr, M., Hofter, E., Becker, A., Pfeiffer, U. J. & Muhlbauer, W. (2002) *Br. J. Plast. Surg.* 55: 635-644) and the measurement of newly created blood vessels in a diabetic patient's eyeballs (Costa, R. A., Calucci, D., Teixeira, L. F., Cardillo, J. A. & Bonomo, P. P. (2003) *Am. J. Opthalmol.* 135: 857-866). ICG receives near infrared rays, having wavelengths ranging from 750-790 nm, and radiates near infrared rays, having longer wavelengths ranging from 800 to 850 nm, and the radiated near infrared rays can be measured using a CCD camera or a spectrometer. Near infrared rays have high penetration power, and thus they can penetrate several centimeters deep into tissue and don't scatter much, with the result that they are the object of extensive research towards human body imaging technology (Morgan, N. Y., English, S., Chen, W., Chernomordik, V., Russo, A., Smith, P. D. & Gandjbakhche, A. (2005) *Acad. Radiol.* 12: 313-323). This method is also used as a technique for structural blood vessel imaging. This method is used for the test of the permeability of newly created blood vessels in a diabetic patient's eyeballs, not for the measurement of tissue perfusion.

The above method is used for an 'ICG elimination test' as well as the above purpose. When ICG is injected into a vein, ICG is attached to protein in a blood vessel, such as albumin, and is rapidly spread into the body via blood vessels. When it is transferred to the liver, it is separated from protein and discharged in the form of bile and excreted from the body finally while the protein is degraded. As a result, the concentration of ICG is rapidly reduced in the blood vessels, so that the intensity of ICG fluorescence signals is reduced to half of the intensity of initial ICG fluorescence signals 4 to 6 minutes later, and is then diminished and deviates from an accurate measurement range. One use of the 'ICG dynamics', in which ICG is rapidly eliminated by the liver, is a liver function test (Sinyoung Kim, et al., (2003) *Kor. J. Lab. Med.,* 23: 88-91), but the ICG dynamics has been known to have shortcomings when applied to in vivo imaging (Sekimoto, M., Fukui, M. & Fujita, K. (1997) *Anaesthesia* 52: 1166-1172). Accordingly, the present inventors have completed the present invention through the ascertainment of the fact that accurate measurement can be conducted in a wide range from a perfusion rate decreased to less than 10% of that of normal perfusion to a perfusion rate increased to greater than that of normal perfusion using the ICG dynamics in the living body.

DISCLOSURE

Technical Problem

An object of the present invention is to provide a method of measuring perfusion in a living body, which enables to provide absolute value of perfusion for respective regions in a wide range from a perfusion rate decreased to less than 10% of normal perfusion to a perfusion rate increased to greater than normal perfusion using the above-described ICG dynamics in a living body, which cannot be conducted in the prior art.

Technical Solution

In order to accomplish the above object, the present invention provides a tissue perfusion analysis apparatus, a method of measuring tissue perfusion and a tissue perfusion measurement apparatus, which calculate a perfusion rate by injecting indocyanine green into a living body and measuring variation in the concentration of the indocyanine green.

Figure 1:
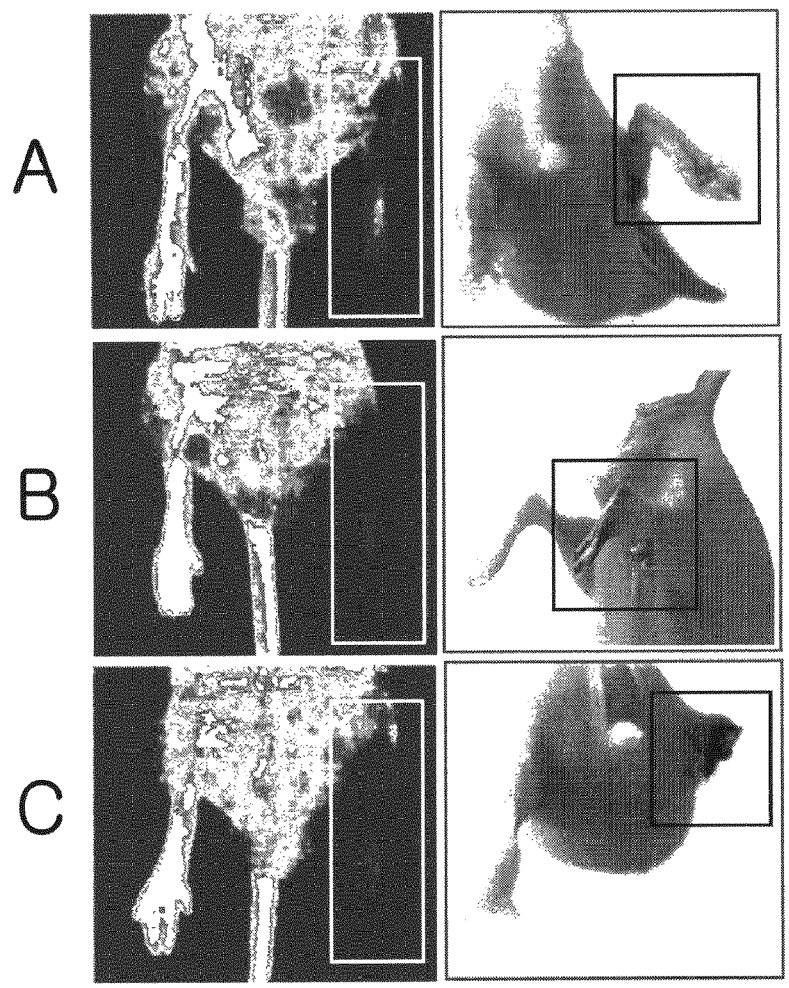
FIG. 1 is a photo showing the fact that there is no correlation between laser Doppler images and the rates of tissue necrosis.

Description of reference numerals of principal elements in the accompanying drawings:
  1: light source, 2: living body stand,
  3: 800~850 nm filter, 4: ICG near infrared ray fluorescence detector, and
  5: ICG image analysis apparatus.

Figure 3:
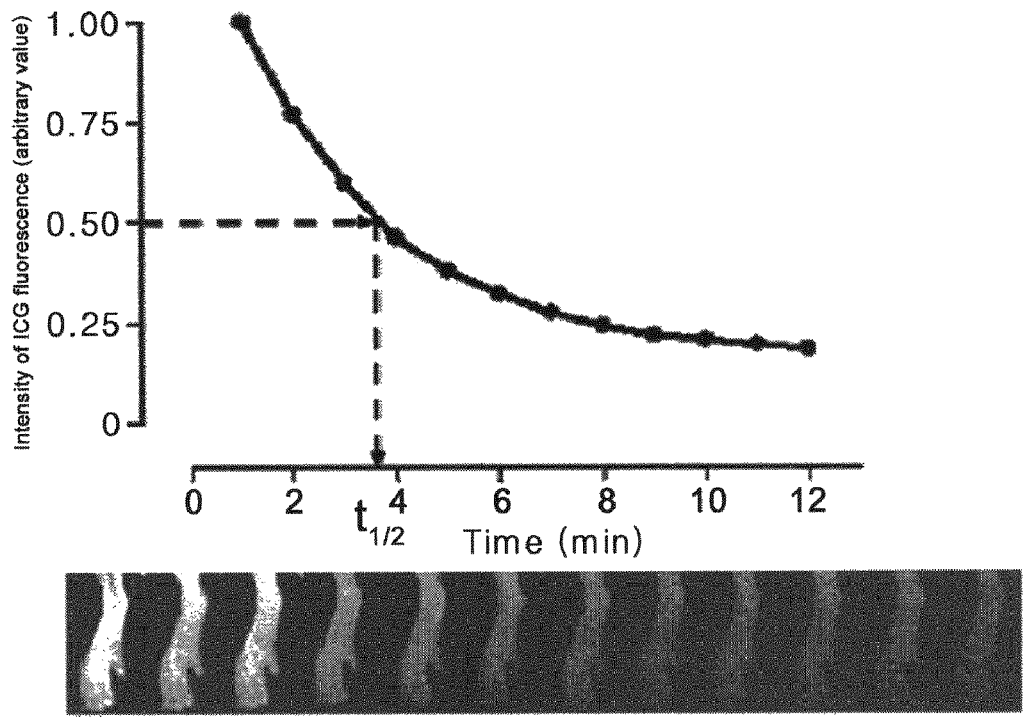

FIG. 3 is a graph (upper side) showing the experimental results of the dynamics of the intensity of ICG fluorescence, directly acquired with the passage of time from the blood in a living body, and a photo (lower side) showing the results of analysis of indocyanine fluorescence.

Figure 4:
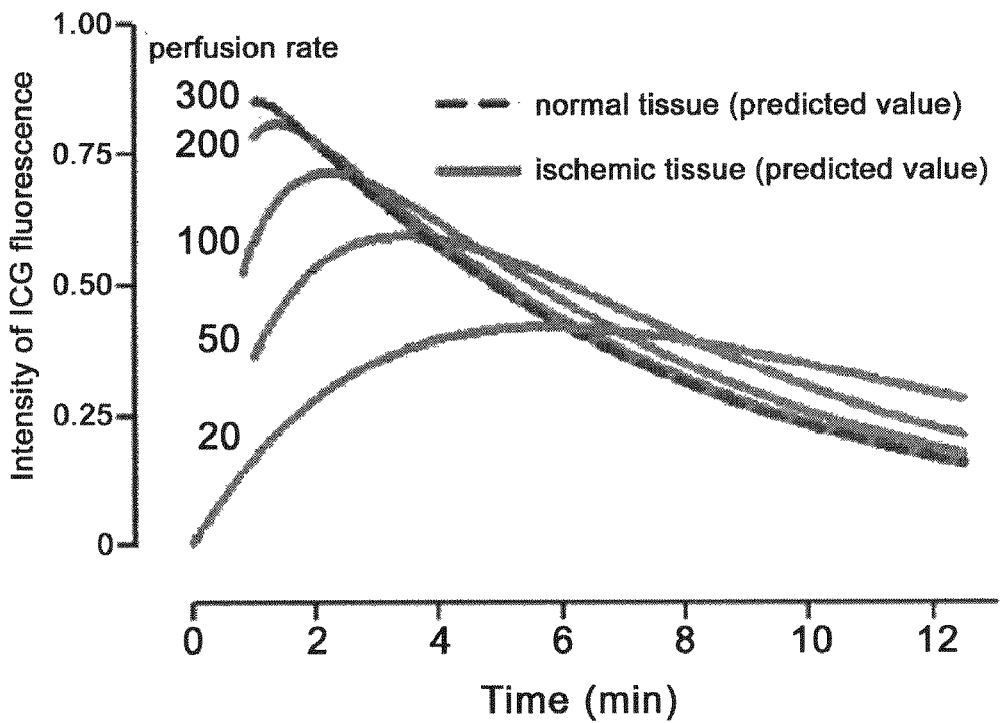

FIG. 4 is a simulation graph showing the mechanism of ICG fluorescence based on the perfusion rates of ischemic tissue.

Figure 5:
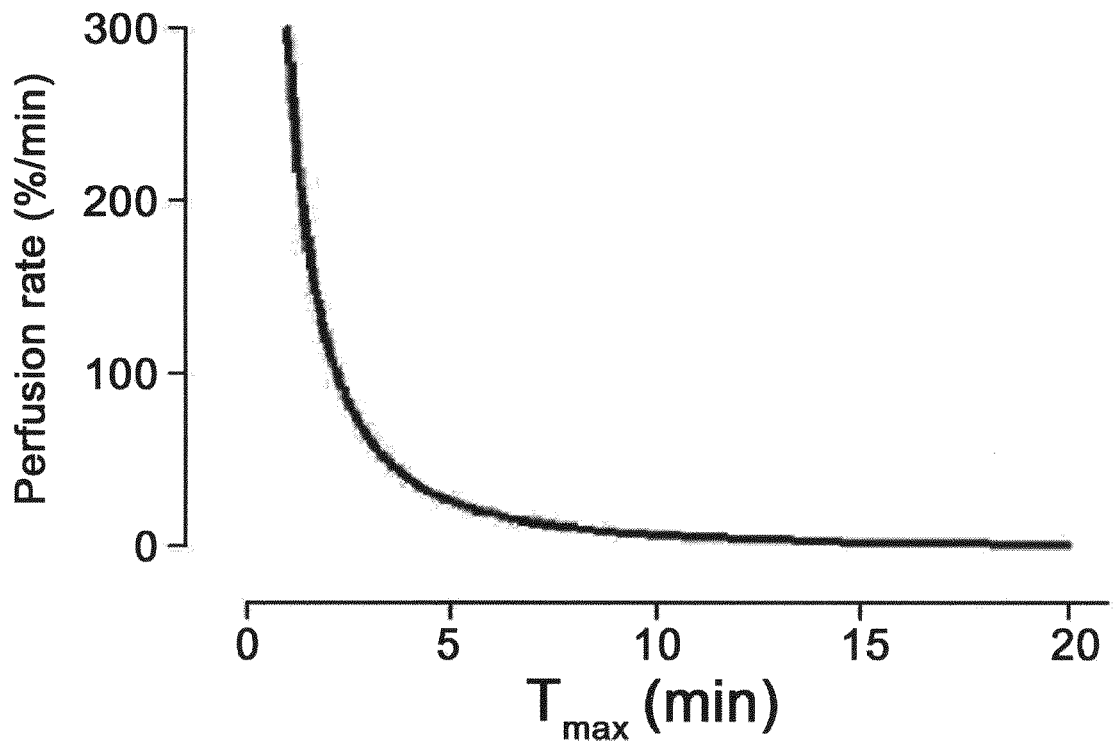

FIG. 5 is a simulation graph showing the relationship between $T_{max}$ and perfusion rates.

Figure 6:
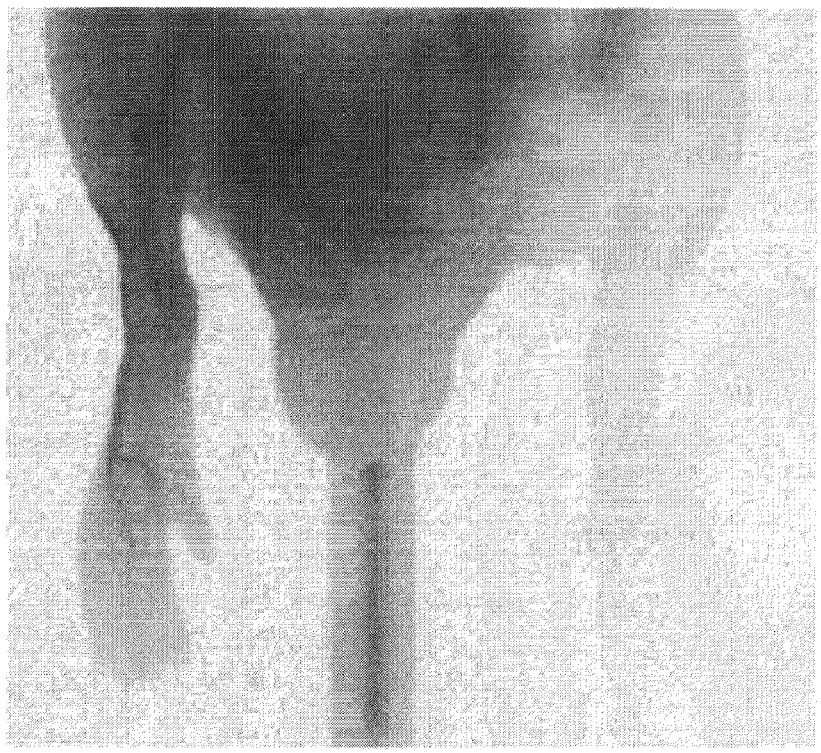

FIG. 6 is an imaging view of a blood vessel acquired after the injection of ICG into the tail vein of a nude mouse.

Figure 7:
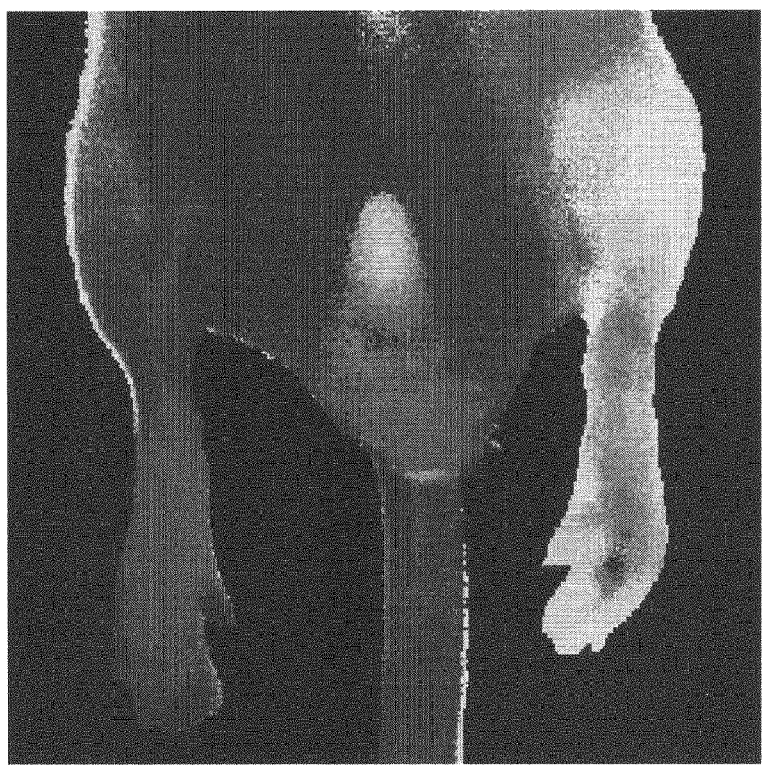

FIG. 7 is an image outputted by mapping perfusion rates as colors, using an ischemia pattern analysis method in a mouse from which a thigh artery has been removed.

Figure 8:
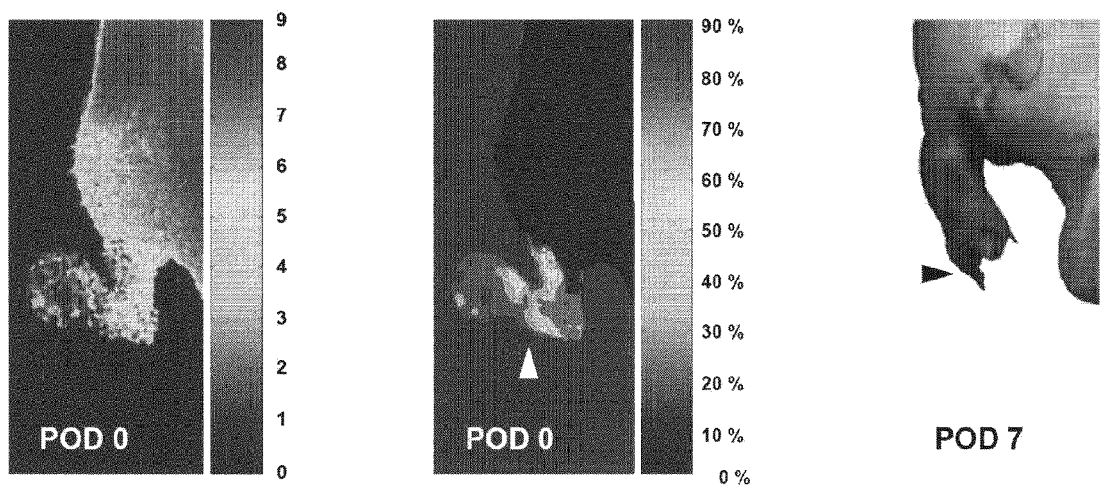

FIG. 8 is a series of images showing the probability of tissue necrosis (center) based on a perfusion map of the ischemia leg indicating ischemia rates measured immediately after an operation (left side), and a photograph showing the actual rates of tissue necrosis seven days after an operation (right side).

Figure 9:
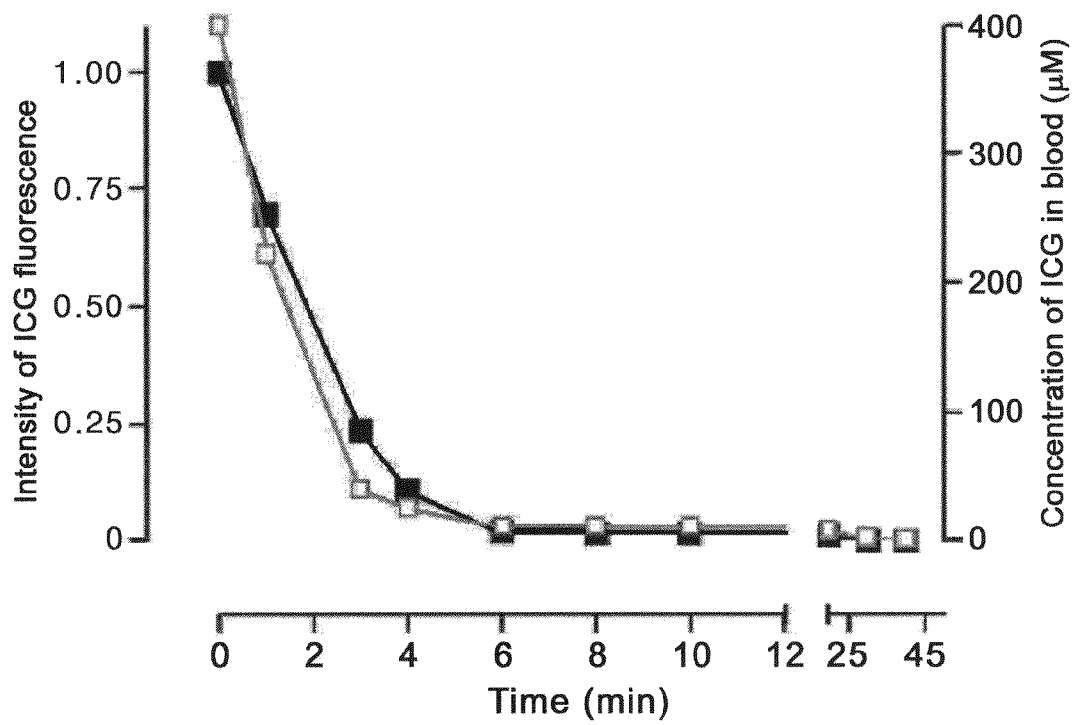
Figure 10:
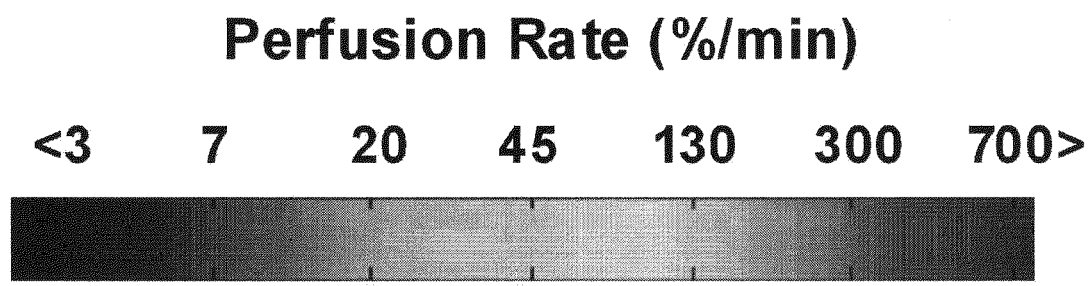

FIG. 9 is a graph showing the experimental results of the dynamics of the intensity of ICG fluorescence in blood collected from a living body; and FIG. 10 is a diagram illustrating an example of the principle of mapping between perfusion rates and colors.

BEST MODE

The present invention will be described in detail below.

The present invention provides an analysis apparatus for measuring the rate of tissue perfusion by injecting indocyanine green (ICG) into a living body and measuring variation in concentration, and then presenting information about the probability of the necrosis of tissue.

The analysis apparatus includes:

1) an input means for receiving signals from a photodetector, 2) a numerical conversion means for processing the input signals into the intensities of fluorescence with the passage of time in a region of interest, 3) a perfusion rate calculation means for calculating the rates of perfusion for respective regions of a tissue using the numerical values, and 4) an output means for outputting the results of the calculation.

In the analysis apparatus, the photodetector is a device for detecting fluorescence in a typical infrared ray, visible ray or ultraviolet ray region. Although not limited to following devices, a photo-detection device, such as a photoresistor, a photovoltaic cell, a photodiode, a photomultiplier tube (PMT), a phototube, a phototransistor, a charge-coupled device (CCD), a pyroelectric detector, a Golay cell, a thermocouple, a thermistor, a complementary metal oxide semiconductor (CMOS) detector or a cryogenic detector, may be used as the photodetector.

It is preferable to use RSC 232, a parallel port, IEEE 1394 or USB as the input means, although the invention is not limited thereto.

The numerical conversion means is operably connected to the input means, and consists of a microprocessor, and operation software embedded therein. The intensity of fluorescence may be numerically converted using a graph, with the intensity of fluorescence being plotted on the y axis and the time of measurement being plotted on the x axis, as shown in FIGS. 3 and 4, but may be numerically converted using some other methods.

The calculation means includes a microprocessor, and operation software embedded therein and configured to drive an algorithm including a calculation equation for calculating perfusion using the numerical value of the intensity of fluorescence and the time of measurement, obtained from the numerical conversion means. The microprocessor may be a microprocessor included in the numerical conversion means, or may be a separate microprocessor.

The calculation uses the fact that the intensity of fluorescence in a normal tissue decreases exponentially with the passage of time of measurement, and the fact that, in the case where ischemia occurs in a tissue that is the target of analysis, the ICG fluorescence particles of normal tissue enter at the perfusion rate of an ischemic tissue and the ICG fluorescence particles of the ischemic tissue exit at the same perfusion rate.

In the present invention, the rate of tissue perfusion can be calculated using the time at which the intensity of fluorescence in a target tissue for analysis is maximized. This uses the fact that, in the case where ischemia occurs in the target tissue for analysis, the time at which the intensity of ICG fluorescence in the ischemic tissue is highest is the point at which the time-differential value is 0. In the present invention, the time is defined as $T_{max}$.

In a specific embodiment of the present invention, $T_{max}$ is obtained using the following method. First, a graph (See FIG. 3), in which images of the ICG fluorescence of a living body, obtained with the passage of time after the injection of ICG using the above-described method, were converted into numerical values with the highest brightness set to 1, was constructed. Since this graph shows a curve that decreases exponentially according with time, calculation can be conducted using the following equation:

$$FI_{nor} = A \times e^{-\frac{t}{\tau}}.$$

In the above equation, $FI_{nor}$ (Fluorescence Intensity normal) means the intensity of ICG fluorescence of normal tissue, 'A' means the intensity of fluorescence obtained from ICG images during the first minute (in the present invention, A is calculated as 1), $\tau$ is defined as $t_{1/2}/\ln 2$ through calculation, and $t_{1/2}$ means the time when the intensity of fluorescence of ICG is half the highest value.

The extent of variation in the intensity of ICG fluorescence in an ischemic tissue, in which the rate of tissue perfusion is lower than that of a normal tissue, can be calculated using the following equation based on the assumption that "the ICG fluorescence particles of the normal tissue ($FI_{nor}$) enter at the rate of perfusion of the ischemic tissue (P) and the ICG fluorescence particles of the ischemic tissue ($FI_{isc}$) exit at the same perfusion rate (P)":

$$FI_{isc} = \frac{PA}{P - 1/\tau}(e^{-\frac{t}{\tau}} - e^{-Pt}).$$

The variation of ICG dynamics, in case when the perfusion rate of the ischemic tissue is lowered, was simulated using the above equation (See FIG. 4). Through the simulation, the result, in which $T_{max}$, which is the time at which the intensity of fluorescence was maximized, increased as the perfusion rate of a tissue decreased, was obtained (See FIG. 5).

The above relationship between $T_{max}$ and the rates of blood perfusion is expressed by the following Equation:

$$-ln\tau - \frac{T_{max}}{\tau} = lnP - PT_{max}. \qquad (1)$$

The rate of tissue perfusion (P) is calculated based on $T_{max}$ using Equation 1.

However, the measurement of the perfusion rate of a tissue based on $T_{max}$ is only an embodiment of the present invention, and it is apparent to those skilled in the art that the scope of protection of the present invention is not limited by the above embodiment. Accordingly, analysis apparatuses for injecting indocyanine green, measuring the concentration of indocyanine green in tissue with the passage of time, and measuring the perfusion rate of the tissue using the mechanism of the dynamics of fluorescence of indocyanine green in tissue fall within the scope of the rights of the present invention, regardless of the algorithm or calculation equation used therein. Meanwhile, in the present invention, the calculated perfusion rates are outputted as a perfusion map wherein the calculated perfusion rates mapped to specific colors. Although it is preferable to use a color gradient for colors corresponding to the rates of perfusion, the present invention is not limited thereto, and a programmer may arbitrarily select a color representation method. The perfusion map as a means for visualizing the rate of tissue perfusion, is outputted through a screen, a printer or the like, and makes an operator of the perfusion rate analysis apparatus of the present invention perceive the rate of tissue perfusion visually and intuitively.

Through the embodiment, a relationship between the perfusion rates, measured using the above-described method, and the probability of future necrosis of a tissue due to ischemia was obtained. In a specific embodiment, the case where the rate of tissue perfusion is about 50%/min is indicated by a yellow color in the perfusion map (See the left side of FIG. 8), and, in the case of this yellow color, the probability of necrosis of a tissue was statistically calculated to be in the range of 0~10%, and it may be colored blue in a tissue necrosis probability map (See the center of FIG. 8 Furthermore, the present invention provides a tissue perfusion measurement apparatus, comprising a stand configured to allow light to pass therethrough, a light source adjustable to be located to radiate light onto an ICG-injected living body which is disposed on the stand, a filter adjustable to be located to filter only near infrared ray wavelengths of 800 to 850 nm from fluorescence signals emitted from the living body under the action of the light source, a detector configured to detect fluorescence light passed through the filter, and an analysis apparatus operably connected to the detector and configured to image light detected by the detector and measure the rates of tissue perfusion through the analysis of the ICG dynamics with the passage of time.

With regard to the light source, a Light Emitting Diode (LED) having a wavelength of 770+/−20 nm, a light source in which a filter having a wavelength of 770+/−20 nm is attached to a white light source, and a laser light source having a wavelength of 770+/−20 nm may be all used as the light source radiating light for detecting ICG fluorescence.

The above-described filter passes only light having a wavelength ranging from 800 to 850 nm therethrough. Using this filter, fluorescence generated in a living body itself is not detected by the detector.

The detector detects near infrared rays having wavelengths ranging from 800 to 850 nm, which are ICG fluorescence signals. An infrared detection camera or a spectrometer may be used as the detector. The detector continuously detects images immediately from the injection of ICG, and transmits signals, capable of exhibiting an ICG dynamics with the passage of time, to the analysis apparatus.

In the present invention, when a Region Of Interest (ROI) of a living body, in which the perfusion rate is desired to be measured, is designated, the intensities of ICG fluorescence with the passage of time are automatically converted into numerical values from continuous ICG image data. Using this, the intensities of ICG fluorescence, measured as in FIG. 3, are processed into temporal and spatial information. $T_{max}$, is obtained based on the data, and then the rates of tissue perfusion are analyzed using the simulation data of FIG. 4, the correlation between $T_{max}$, of FIG. 5 and the rates of tissue perfusion, and the Equation 1. Furthermore, using the results of the analysis, a tissue perfusion map (See FIG. 7 and the left side of FIG. 8) and a tissue necrosis rate prediction map (See the center of FIG. 8) are provided. This prediction exhibited a high prediction level in the embodiment of the present invention (See the right side of FIG. 8).

In order to measure an ICG dynamics in a living body using the above measuring apparatus, ICG must be injected through an intravenous injection and variation in the concentration of ICG in tissue with the passage of time must be detected and analyzed. The variation in the concentration of ICG in tissue may be measured through the acquisition of a blood sample, through the direct acquisition of a near infrared ray image of the tissue, or using a spectroscopic technique.

Furthermore, the present invention provides a method of measuring the rate of tissue perfusion, comprising:

1) detecting sequentially concentration of ICG until the concentration of ICG is sufficiently decreased by injecting the ICG into a living body, radiating light onto the living body using a light source, and measuring the intensities of fluorescence, generated in the living body with the passage of time after the injection, using a photodetector;

2) processing the sequential concentration of ICG in the living body detected in the step 2 into numerical data by converting the intensities of ICG fluorescence into numerical values for respective regions and respective times; and 3) calculating the rates of perfusion from the numerical data.

In an embodiment, it is preferred that the method of measuring the rates of tissue perfusion further comprises the step of outputting the calculated perfusion rates as a perfusion map. It is preferred that the perfusion map is constructed by painting particular pixels with respective colors corresponding to the rates of perfusion according to a gradient map.

According to another embodiment, the present invention provides a method of measuring the rates of tissue perfusion, comprising:

1) detecting sequentially concentration of ICG until the concentration of ICG is sufficiently decreased by injecting the ICG into a living body, radiating light onto the living body using a light source, and measuring intensities of fluorescence, generated in the living body with the passage of time, using a photodetector and obtaining an ICG blood vessel image diagram using the intensities of fluorescence;

2) acquiring $T_{max}$ by analyzing dynamics of the intensities of ICG fluorescence per respective pixel in the ICG blood vessel image diagram; and 3) calculating the rates of perfusion rate based on the $T_{max}$.

In this case, it is preferred that the method of measuring the rates of tissue perfusion further comprises the step of outputting the calculated perfusion rates as a perfusion map. It is preferred that the perfusion map is constructed by painting particular pixels with respective colors corresponding to the rates of perfusion according to a color gradient map, wherein the rates of perfusion is calculated through the analyzed data.

Furthermore, the present invention provides a method of predicting the rate of tissue necrosis, comprising representing a tissue necrosis probability map, indicating the probability of necrosis of a tissue, based on the rates of tissue perfusion acquired using the above-described measurement method, as a result (See the right side of FIG. 8).

In the measurement method, with regard to the light source, an LED having a wavelength of 770+/−20 nm, a light source in which a filter having a wavelength of 770+/−20 nm is attached to a white light source, and a laser light source, having a wavelength of 770+/−20 nm, may all be used as a light source radiating light for detecting ICG fluorescence. Any device using the above-described photo-detection device may be used as the photodetector. Although the photodetector is not limited, the photodetector must detect near infrared rays having wavelengths ranging from 800 to 850 nm, which are ICG fluorescence signals, and an infrared detection camera or a spectrometer may be used as the photodetector. The photodetector sequentially detects images immediately after an injection of ICG, and transmits signals, capable of exhibiting an ICG dynamics with the passage of time, to the analysis apparatus.

Meanwhile, with regard to fluorescence emitted from a living body, it is preferred that fluorescence generated from a living body itself is not detected using a filter capable of passing only light having wavelengths ranging from 800 to 850 nm therethrough.

It is preferred that the data processing step and the perfusion rate analyzing step are performed using a microprocessor and software embedded in the microprocessor, or stored in external storage, such as a hard disk drive, an optical drive or a flash memory. This software is not limited to a specific algorithm, as described above, and may be implemented through one of various platforms, such as Windows series operating systems, for example, Microsoft Windows XP, 2000, Me, 98 and 95, Linux, OS/2, and Unix.

Although the correlation coefficient at the perfusion rate analysis step is not limited thereto, it is preferred that the correlation coefficient is the time at which the intensity of ICG fluorescence of a target tissue to be analyzed (ischemic tissue) is maximized.

Although the acquisition of $T_{max}$ at the step of calculating perfusion rates from the dynamics of ICG fluorescence intensity of the target tissue (ischemic tissue) does not limit the method of analyzing the perfusion rates, it is preferable to perform calculation using the principle in which the time $T_{max}$, at which the differential value of the intensity of fluorescence is 0, is proportional to the perfusion rate in the target tissue.

The step 3 may be embodied by the following steps: perfusion rates of region of interest (ROI) according to (a) average data of pixels of particular regions, (b) respective pixels, or (c) respective ROIs representing perfusion rates; and representing the perfusion rates using a perfusion map by illustrating the perfusion rates for the ROI with corresponding colors designated according to the perfusion rates. The above process may be performed by calculations using software having an appropriate algorithm and loaded on a microprocessor and a display through an output device of a computer. FIG. 7 shows an example of the perfusion map, which may be acquired by sequentially obtaining fluorescence images with the passage of time after injecting ICG, measuring the perfusion rates through the analysis of the ICG fluorescence dynamics of respective pixels, and painting the pixels with colors corresponding to the measured perfusion rates. An example of matching between the perfusion rates and colors is illustrated in FIG. 10.

Although the output device is not limited thereto, it is preferred that the output device is a monitor, a printer or a plotter. It is possible to store data in various graphic formats using an external storage device.

The present inventors carried out a surgical operation of removing an artery and vein from the thigh of a leg of a nude mouse, acquired ICG images using the above-described method, and obtained the $T_{max}$ value. Since the rate of tissue necrosis was greatly affected by the rate of tissue perfusion, whether the 'precise perfusion rates' were measured was evaluated through the observation of rates of tissue necrosis. As a result, as shown in FIG. 8, the method of the present invention showed the significant relationship between measured perfusion values and the rates of tissue necrosis. This indicates that measurement can be performed in the case where the perfusion rate is decreased to 0.04~50%/min (the perfusion rate of a normal leg: 300%/min), unlike the measurement using Doppler imaging (refer to FIG. 1), that is, a comparative example, in which a subtle difference in the considerably decreased 'perfusion rate' could not be measured.

MODE FOR INVENTION

The present invention will be described in detail below in conjunction with embodiments.

However, the following embodiments are only to illustrate the present invention, but do not limit the content of the present invention.

COMPARATIVE EXAMPLE 1

Prediction for Tissue Necrosis through Doppler Imaging

In FIG. 1, showing the present inventors' experimental data, the three left views thereof show data obtained through laser Doppler imaging one to four days after a surgical operation of removing an artery and vein from the thigh of one leg of a mouse so as to construct a blood perfusion reduction model, and the right view thereof shows the rate of necrosis of the leg tissue a week thereafter. With regard to the rates of tissue necrosis, the case A shows no necrosis, the case B shows necrosis reaching the center of the sole of the foot, and the case C shows necrosis reaching the ankle, and the rate of necrosis is proportional to the rate of tissue perfusion (Helisch, A. et al., (2006) Arterioscler. Thromb. Vasc. Biol. 26: 520-526, the case A shows 160% of normal perfusion, the case B shows 20% of normal perfusion, and the case C shows 5% of normal perfusion). Respective pieces of Doppler imaging data corresponding to the cases did not exhibit any difference in tissue perfusion between the cases.

EXAMPLE 1

Establishment of Method of Measuring Perfusion Using ICG

The present inventors derived an equation through the following steps so as to establish a method of measuring perfusion based on the ICG concentration dynamics in blood.

FIG. 9 is a graph that is obtained by injecting ICG (1.5 mg/kg, Sigma, USA) into a vein, collecting blood over time, measuring the intensities of ICG fluorescence, and converting the intensities into the concentrations of ICG in blood. The closed squares of the graph indicate the intensities of ICG fluorescence, while the open squares thereof indicate the concentrations of ICG in blood. FIG. 3 shows variation in ICG fluorescence over a period of time from 1 minute to 12 minutes after the injection of ICG. That is, in FIG. 3, an image of the ICG fluorescence of a living body acquired with the passage of time is converted into numerical values, with the highest brightness set to 1, and is represented in the form of a graph. When variation in ICG in normal tissue is formulated using a graph acquired from a normal tissue, as shown in FIG. 3, the graph decreases exponentially with respect to time, and thus the following formulation can be realized:

$$FI_{nor} = A \times e^{-\frac{t}{\tau}},$$

Wherein the $FI_{nor}$ (Fluorescence Intensity normal) is the intensity of ICG fluorescence in the normal tissue, A is the intensity of fluorescence obtained from an ICG image for a first minute (in the present invention, A is calculated as 1), and τ is defined as $t_{1/2}$/ln 2 through calculation. Furthermore, $t_{1/2}$ is the time at which the intensity of ICG fluorescence is half of the highest value.

A simulation was made under the expectation that, when tissue perfusion decreases, the speed of dispersion of ICG decreases, with the result that variation in the intensity of ICG fluorescence differs from that of normal tissue. In this case, the 'perfusion rate' is 'the rate at which blood in a region of interest is exchanged for blood in the other regions for one minute with respect to the total amount of blood.' The unit of the perfusion rate is %/min, and the 'perfusion rate' of a normal leg was calculated as 300%/min. The rate of variation in the intensity of ICG fluorescence with the passage of time in an ischemic tissue, the perfusion rate of which is lower than in a normal tissue, is expressed by the following equation on the assumption that "ICG fluorescence particles $FI_{nor}$ in the normal tissue enter at the perfusion rate P of the ischemic tissue, and ICG fluorescence particles $FI_{isc}$ in the ischemic tissue exit at the same perfusion rate P."

The following equation is given for $FI_{isc}$ ($FI_{ischemia}$) as follows:

$$FI_{isc} = \frac{PA}{P - 1/\tau}(e^{-\frac{t}{\tau}} - e^{-Pt}).$$

In this case, the simulation graph of FIG. 4 is obtained by substituting a perfusion rate of 20-300%/min for P. In this graph, as the perfusion rate decreases, the maximum value of the intensity of ICG fluorescence decreases, and the time at which the intensity of ICG fluorescence is maximized is delayed.

An actual ICG fluorescence intensity graph differs from a simulated graph. The decrease in the intensity of ICG fluorescence in a normal tissue varies with the state of a living body, with the result that absolute comparison is possible only when the fluorescence in an ischemic tissue is corrected. As a result, a 'correlation coefficient', which is a standard criterion for obtaining 'perfusion rates' from respective pieces of experimental data, is required, and, in the present invention, $T_{max}$ is selected as the correlation coefficient. $T_{max}$ is the time at which the differential value of the ICG fluorescence intensity dynamics of an ischemic tissue is 0.

Since $T_{max}$, which is the time at which the intensity of ICG fluorescence in an ischemic tissue is highest, is the point at which the time-differential value is 0, the following equation can be given:

$$\frac{dFI_{isc}(T_{max})}{dt} = 0, \quad \text{and}$$

-continued $$\frac{dFI_{isc}(T_{max})}{dt} = \frac{PA}{P - t/\tau}\left[-\frac{1}{\tau}e^{-\frac{T_{max}}{\tau}} + Pe^{-PT_{max}}\right] = 0.$$

These can be summarized as follows:

$$-\ln\tau - \frac{T_{max}}{\tau} = \ln P - PT_{max}. \tag{1}$$

A graph for $T_{max}$ and the 'perfusion rate' is shown in FIG. 5.

EXAMPLE 2

Figure 2:
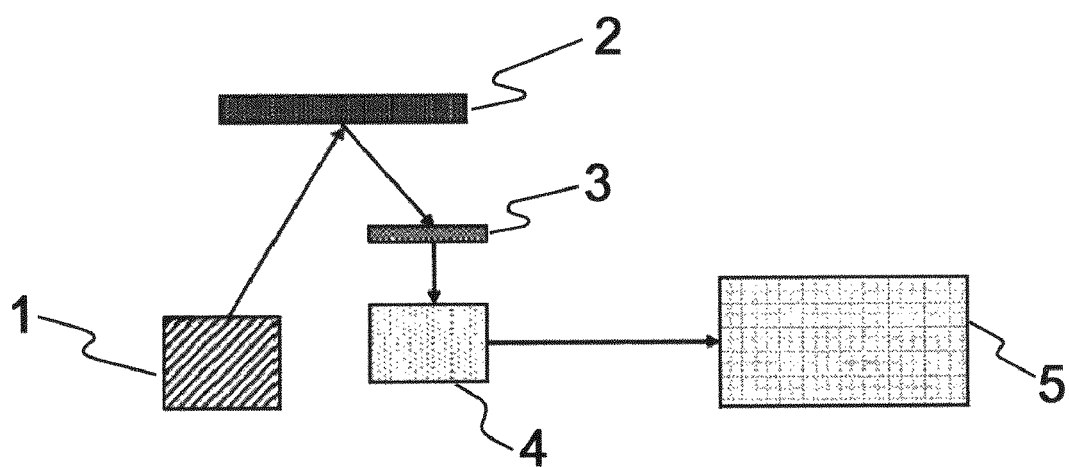
FIG. 2 is a schematic diagram showing the overall construction for detecting ICG fluorescence signals.

Measurement of Perfusion Using Indocyanine Green and the Construction of Perfusion Map and Tissue Necrosis Probability Map Based on Correlation Coefficient The present inventors constructed a blood perfusion reduction model to obtain ICG images in an actual ischemic tissue. A surgical operation of removing an artery and vein from one leg of each of 50 nude mice (Charlse liver Japan, Inc.) was carried out, ICG images were acquired using the measurement apparatus of FIG. 2 four hours after the surgical operation, and the perfusion rates of tissues were obtained using the above-described method.

The obtained perfusion rates of tissues were arranged in a perfusion map (the left side of FIG. 8). In FIG. 8, a perfusion rate of 300%/min corresponds to 9 in the perfusion map, 0%/min corresponds to 0.

Since the rate of tissue necrosis is considerably affected by the rate of tissue perfusion, whether a 'perfusion rate' has been precisely measured can be evaluated through the observation of the rate of tissue necrosis. The rates of tissue necrosis of 50 laboratory mice were observed seven days after operations (the right side of FIG. 8), and the relationship between perfusion rates and the rates of tissue necrosis, which were obtained four hours after the operations, was statistically analyzed using the statistical data. As a result of the analysis, it was ascertained that the probability of tissue necrosis corresponding to a perfusion rate of 50%/min fell within a range of 0~10%, and the probability of tissue necrosis corresponding to a perfusion rate ranging from 15 to 20%/min fell within a range of 75 to 80%. The present inventors assigned a red color to the case where the probability of tissue necrosis was 1 and a blue color to the case where the probability of tissue necrosis was 0, and constructs a necrosis probability map for the tissue using a color gradient between the cases (the center of FIG. 8). The result, in which the constructed tissue necrosis probability map corresponded to the actual rates of tissue necrosis, was acquired.

The result exhibited the fact that the probability of necrosis of tissue increased as the perfusion rate measured using the method decreased, and thus verified the precision of 'perfusion rates' acquired using the method. This means that it was impossible to measure a subtle difference in considerably decreased 'perfusion rate' using the conventional technology, as shown in FIG. 1, but it is possible to perform measurement using the method of the present invention in the case where the perfusion rate is decreased to 0.04-50%/min (the perfusion rate of a normal leg: 300%/min). This coincides with the rate of tissue necrosis, which means that the method of the present invention has an ability to predict the rate of tissue necrosis.

INDUSTRIAL APPLICABILITY

According to the method of the present invention, it is possible to measure perfusion rates precisely in a wide range from a perfusion rate decreased to less than 10% to a perfusion rate increased to the normal perfusion rate, and it is possible to predict the rate of tissue necrosis based on the perfusion rate. In addition, since it is possible to measure variation in blood perfusion, the present invention can be used for the diagnosis of blood perfusion rate and the measurement of variation in perfusion rate after an operation in a region in which the necrosis of a tissue does not appear in actual clinical situations. Furthermore, the present invention can be used for a blood vessel endothelial cell function test by comparing an ICG fluorescence dynamics when the ICG is injected in a normal blood vessel with an ICG fluorescence dynamics varied by drugs inducing activation of blood vessel endothelial cells or external pressure.

The invention claimed is:

1. A computer for measuring a rate of tissue perfusion using time-series analysis of fluorescence images of indocyanine green (ICG), comprising:
   1) an input module configured to receive signals from a photodetector,
   2) a numerical conversion module configured to process input signals from the input module into numerical values, said input signals comprising intensities of fluorescence over time in a region of interest,
   3) a rate calculation module configured to calculate rates of tissue perfusion with using the numerical values and an equation representing dynamics of the ICG, and
   4) an output module configured to output results of the calculation,
   wherein the equation representing dynamics of the ICG is either $$FI_{isc} = \frac{PA}{P - 1/\tau}\left(e^{-\frac{t}{\tau}} - e^{-Pt}\right) \text{ or } -ln\tau - \frac{T_{max}}{\tau} = lnP - PT_{max},$$

wherein the $FI_{isc}$ (Fluorescence Intensity ischemia) is an intensity of ICG fluorescence of a measurement target tissue, the P is a rate of tissue perfusion, the A is an intensity of fluorescence obtained from ICG image during the first 1 minute, the $\tau$ is $t_{1/2}/ln2$, the $t_{1/2}$ is a time at which the intensity of ICG fluorescence is half of a highest value and the $T_{max}$ is a time at which the intensity of ICG fluorescence in an ischemic tissue is highest.

2. An apparatus for measuring tissue perfusion, comprising: a stand configured to allow light to pass therethrough, a light source adjustable to be located to radiate light onto an ICG-injected tissue disposed on the stand, a filter adjustable to be located to filter only near infrared ray wavelengths of 800 to 850 nm from fluorescence signals emitted from the living body under the action of the light source, a detector configured to detect fluorescence light passed through the filter, and the computer of claim 1 operably connected to the detector and configured to image light detected by the detector and measure the rates of tissue perfusion through analysis of the ICG dynamics with the passage of time.

3. A method of measuring a rate of tissue perfusion, comprising:
   1) detecting sequentially a concentration of ICG until the concentration of ICG is decreased to a lowest level by injecting the ICG into a living body, radiating light onto the living body using a light source, and measuring intensities of ICG fluorescence generated in the living body with the passage of time after the injection using a photodetector;
   2) processing the sequential concentration of ICG in the living body detected in the step 1) into numerical data by converting the intensities of ICG fluorescence into numerical values for respective regions and respective times; and
   3) calculating the rates of perfusion from the numerical values,
   wherein the perfusion rates are calculated using the following equation:

$$FI_{isc} = \frac{PA}{P - 1/\tau}\left(e^{-\frac{t}{\tau}} - e^{-Pt}\right) \text{ or } -ln\tau - \frac{T_{max}}{\tau} = lnP - PT_{max},$$

wherein the $FI_{isc}$ (Fluorescence Intensity ischemia) is an intensity of ICG fluorescence of a measurement target tissue, the P is a rate of tissue perfusion, the A is an intensity of fluorescence obtained from ICG image during the first 1 minute, the $\tau$ is $t_{1/2}/ln2$, the $t_{1/2}$ is a time at which the intensity of ICG fluorescence is half of a highest value and the $T_{max}$ is a time at which the intensity of ICG fluorescence in an ischemic tissue is highest.

4. The method as set forth in claim 3, further comprising outputting the calculated perfusion rates as a perfusion map.

5. The method as set forth in claim 4, wherein the perfusion map is constructed by coloring particular pixels with respective colors corresponding to the rates of perfusion according to a color gradient map.

6. A method of measuring a rate of tissue perfusion, comprising:
   1) detecting sequentially a concentration of ICG until the concentration of ICG is decreased to a lowest level by injecting the ICG into a living body, radiating light onto the living body using a light source, and measuring intensities of fluorescence generated in the living body with the passage of time using a photodetector and obtaining an ICG blood vessel image diagram using the intensities of fluorescence;
   2) acquiring $T_{max}$ by analyzing dynamics of the intensities of ICG fluorescence per respective pixel in the ICG blood vessel image diagram; and
   3) calculating the rates of perfusion rate based on the $T_{max}$,
   wherein the perfusion rates are calculated using the following equation:

$$-ln\tau - \frac{T_{max}}{\tau} = lnP - PT_{max},$$

wherein the P is a perfusion rate, and the $\tau$ is $t_{1/2}/ln2$, the $t_{1/2}$ is a time at which the intensity of ICG fluorescence is half of a highest value and the $T_{max}$ is a time at which the intensity of ICG fluorescence in an ischemic tissue is highest.

7. The method as set forth in claim 6, further comprising outputting the calculated perfusion rates as a perfusion map.

8. The method as set forth in claim 7, wherein the perfusion map is constructed by coloring particular pixels with respective colors corresponding to the rates of perfusion according to a color gradient map.

9. A method of predicting a rate of tissue necrosis, comprising outputting a tissue necrosis probability map by indicating the probability of necrosis of a tissue based on the rates of tissue perfusion acquired using the method set forth in claim 3.

10. The method as set forth in claim 4, wherein the perfusion map is constructed using a method of acquiring perfusion rates of region of interest (ROI) according to (a) average data of pixels of particular regions, (b) respective pixels, or (c) respective ROIs representing perfusion rates; and representing the perfusion rates using the perfusion map by illustrating the perfusion rates for the ROI with corresponding colors designated according to the perfusion rates.

11. A method of predicting a rate of tissue necrosis, comprising outputting a tissue necrosis probability map by indicating the probability of necrosis of a tissue based on the rates of tissue perfusion acquired using the method set forth in claim 6.

12. The method as set forth in claim 7, wherein the perfusion map is constructed using a method of acquiring perfusion rates of region of interest (ROI) according to (a) average data of pixels of particular regions, (b) respective pixels, or (c) respective ROIs representing perfusion rates; and representing the perfusion rates using the perfusion map by illustrating the perfusion rates for the ROI with corresponding colors designated according to the perfusion rates.

\* \* \* \* \*